US012787866B2

(12) United States Patent
Chen

(10) Patent No.: US 12,787,866 B2

(45) Date of Patent: Nov. 3, 2026

(54) SEMICONDUCTOR PACKAGE

(71) Applicant: Advanced Semiconductor Engineering, Inc., Kaohsiung (TW)

(72) Inventor: Ying-Chung Chen, Kaohsiung (TW)

(73) Assignee: Advanced Semiconductor Engineering, Inc., Kaohsiung (TW)

( * ) Notice: Subject to any disclaimer, the term of this patent is extended or adjusted under 35 U.S.C. 154(b) by 885 days.

(21) Appl. No.: 17/950,041

(22) Filed: Sep. 21, 2022

(65) Prior Publication Data

US 2024/0096862 A1 Mar. 21, 2024

(51) Int. Cl.

| | |
|---|---|
| ***H10W 90/00*** | (2026.01) |
| ***G01F 1/66*** | (2022.01) |
| ***G01L 11/02*** | (2006.01) |
| ***G01N 33/00*** | (2006.01) |
| ***H10F 77/40*** | (2025.01) |
| ***H10F 77/50*** | (2025.01) |
| ***H10H 20/85*** | (2025.01) |
| ***H10H 20/856*** | (2025.01) |
| *G01F 25/10* | (2022.01) |
| *G01L 27/00* | (2006.01) |

(52) U.S. Cl.

CPC ............ *H10W 90/00* (2026.01); *G01F 1/662* (2013.01); *G01L 11/02* (2013.01); *G01N 33/0022* (2013.01); *H10F 77/413* (2025.01); *H10F 77/50* (2025.01); *H10H 20/8506* (2025.01); *H10H 20/856* (2025.01); *G01F 25/15* (2022.01); *G01L 27/002* (2013.01); *G01N 33/0006* (2013.01)

(58) Field of Classification Search

CPC ....... H01L 25/165; H01L 23/02; H01L 25/16; H01L 25/0655; H01L 25/167; G01F 1/6845; G01F 25/15; G01F 1/662; G01N 33/0006; G01N 33/0022; G01L 27/002; G01L 11/02; H10H 20/8506; H10H 20/856; H10F 77/50; H10F 77/413

See application file for complete search history.

(56) References Cited

U.S. PATENT DOCUMENTS 9,091,577 B2 * 7/2015 Speldrich .................. G01F 5/00
2022/0115245 A1 * 4/2022 Narayanasamy ............................ H01L 23/49562

FOREIGN PATENT DOCUMENTS

CN 104568784 A * 4/2015
CN 104568784 B 8/2017
CN 114105079 A * 3/2022 ......... B81C 1/00261
TW 201734412 A * 10/2017 ............... G01F 1/66

* cited by examiner

*Primary Examiner* — Kretelia Graham
*Assistant Examiner* — Nkechinyere Esiaba
(74) *Attorney, Agent, or Firm* — Foley & Lardner LLP

(57) ABSTRACT

A semiconductor package and a lid structure are disclosed. The semiconductor package includes a carrier, a lid structure, a first die, and a second die. The lid structure is disposed over the carrier and includes a gas inlet and a gas outlet. The first die is disposed over the carrier. The second die is disposed over the carrier. The lid structure includes a first protrusion pattern protruding toward the carrier and extending between the first die and the second die.

7 Claims, 21 Drawing Sheets

1

1

7

SEMICONDUCTOR PACKAGE

BACKGROUND

1. Field of the Disclosure

The present disclosure relates to a semiconductor package, and in particular to a semiconductor package including a lid structure.

2. Description of the Related Art

The detection system of gas flow normally requires different types of sensors. However, the conventional technique relates to manufacturing these sensors separately, which causes the size of the system to be adversely bulky.

SUMMARY

In some embodiments, a semiconductor package includes a carrier, a lid structure, a first die, and a second die. The lid structure is disposed over the carrier and includes a gas inlet and a gas outlet. The first die is disposed over the carrier. The second die is disposed over the carrier. The lid structure includes a first protrusion pattern protruding toward the carrier and extending between the first die and the second die.

In some embodiments, a semiconductor package includes a carrier and a lid structure. The lid structure includes a gas inlet, a gas outlet, and a first surface facing the carrier. The first surface of the lid structure and the carrier is configured to collectively define a first pathway and a second pathway. The first pathway and the second pathway both connect the gas inlet and the gas outlet.

In some embodiments, a semiconductor package includes a carrier and lid structure. The lid structure includes a gas inlet and a gas outlet arranged along a first direction. The lid structure and the carrier collectively define a first pathway connecting the gas inlet and the gas outlet. A first sidewall of the first pathway has a second height and a second sidewall of the first pathway opposite to the first sidewall has a second height. The first height is different from the second height.

BRIEF DESCRIPTION OF THE DRAWINGS

Aspects of some embodiments of the present disclosure are readily understood from the following detailed description when read with the accompanying figures. It is noted that various structures may not be drawn to scale, and dimensions of the various structures may be arbitrarily increased or reduced for clarity of discussion.

DETAILED DESCRIPTION

Figure 1:
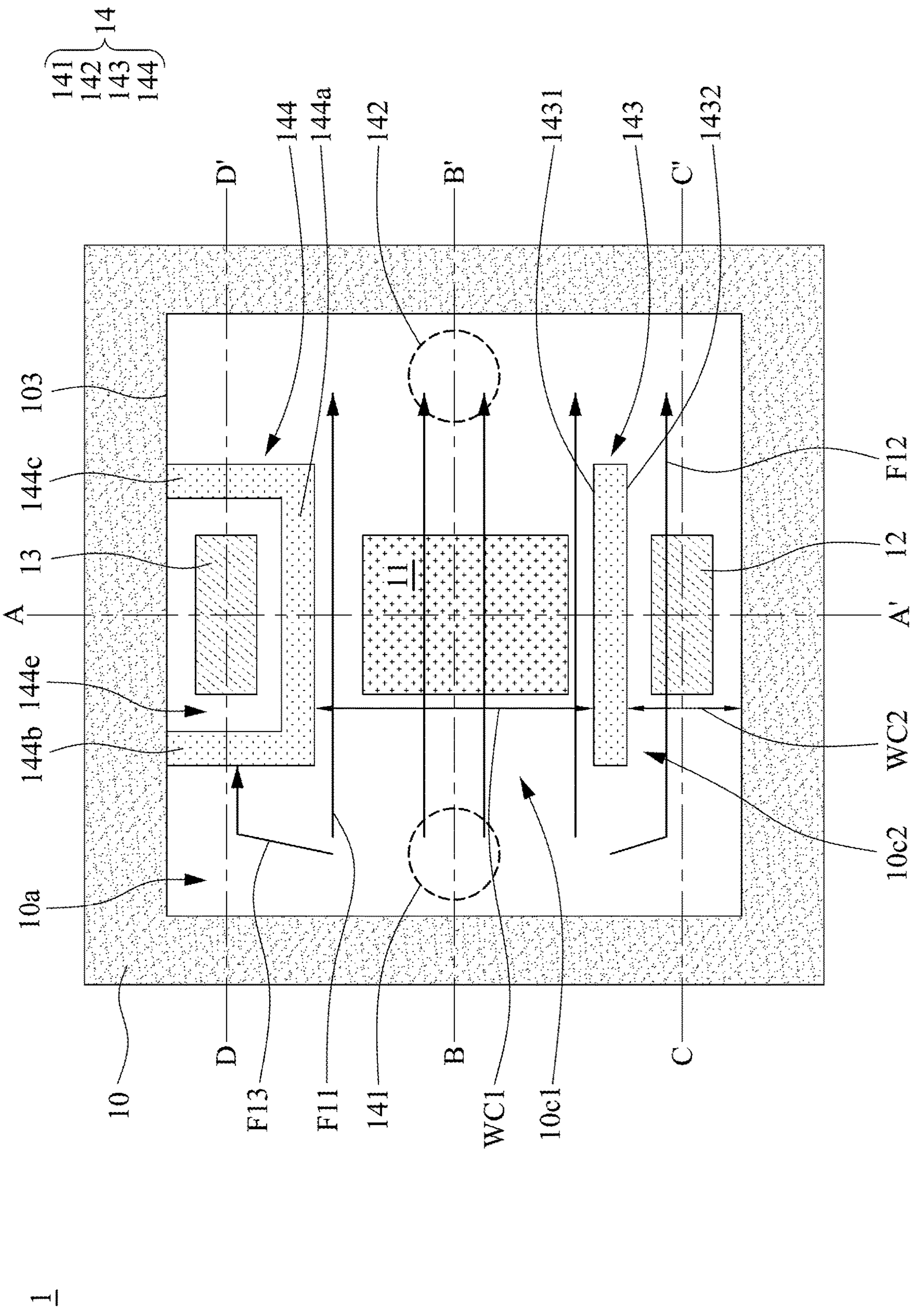
FIG. 1 is a perspective view of a semiconductor package in accordance with some embodiments of the present disclosure.

Common reference numerals are used throughout the drawings and the detailed description to indicate the same or similar components. Embodiments of the present disclosure will be readily understood from the following detailed description taken in conjunction with the accompanying drawings.

The following disclosure provides many different embodiments, or examples, for implementing different features of the provided subject matter. Specific examples of components and arrangements are described below to explain certain aspects of the present disclosure. These are, of course, merely examples and are not intended to be limiting. For example, the formation of a first feature over or on a second feature in the description that follows may include embodiments in which the first and second features are formed or disposed in direct contact, and may also include embodiments in which additional features may be formed or disposed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Figure 2:
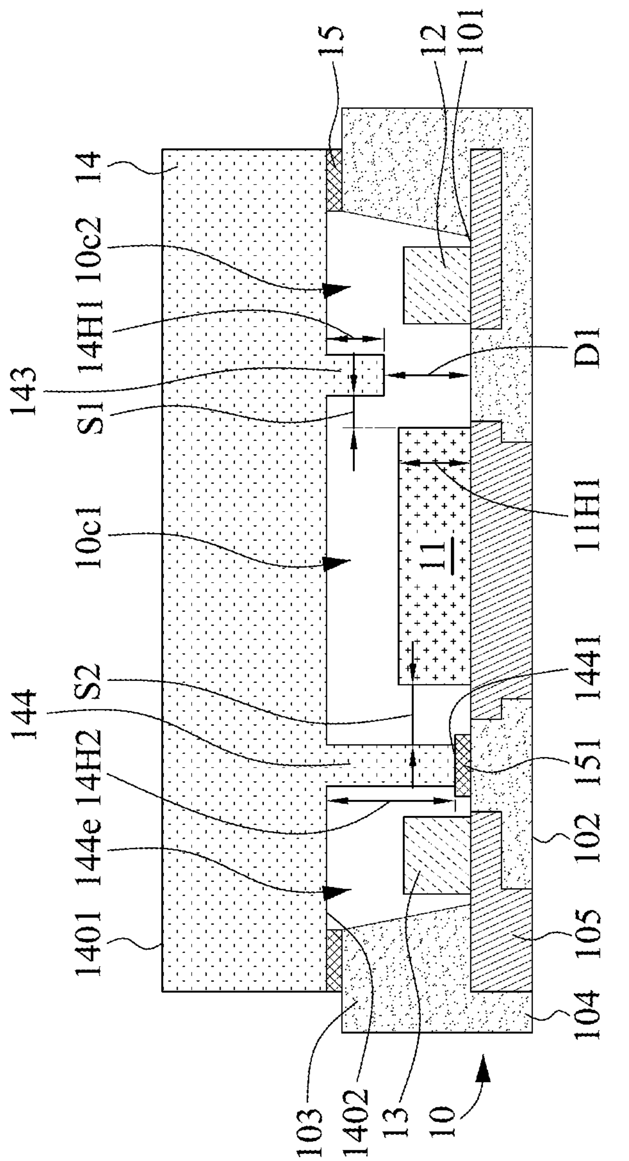
FIG. 2 is a cross-sectional view along the line A-A' in FIG. 1 in accordance with some embodiments of the present disclosure.

FIG. 1 is a perspective view of a semiconductor package 1 in accordance with some embodiments of the present disclosure. FIG. 2 is a cross-sectional view along the line A-A' in FIG. 1 in accordance with some embodiments of the present disclosure.

The semiconductor package 1 may include a carrier 10, a die (or a semiconductor chip) 11, a die (or a semiconductor chip) 12, a die (or a semiconductor chip) 13, and a lid structure 14.

Referring to FIG. 1, the carrier 10 may surround the lid structure 14. The carrier 10 may be disposed below the lid structure 14. The carrier 10 and the lid structure 14 may collectively define a cavity (or a chamber) 10*a* to accommodate one or more of the dies (e.g., the die 11, the second die 12, and third die 13. The carrier 10 and the lid structure 14 may collectively define a pathway (or an air channel) 10*c*1 and a pathway (or an air channel) 10*c*2 to respectively accommodate the die 11 and the die 12. A diameter of the pathway 10*c*1 may be different from a diameter of the pathway 10*c*2. In some embodiments, the diameter of the pathway 10*c*1 is a width WC1 of the pathway 10*c*1 and the diameter of the pathway 10*c*2 is a width WC2 of the pathway 10*c*2. For example, a width WC1 of the pathway 10*c*1 may be larger than a width WC2 of the pathway 10*c*2. Referring to FIG. 2, the pathway 10*c*1 and the pathway 10*c*2 may have substantially the same height (e.g., between the carrier 10 and the lid structure 14). The diameter of the pathway 10*c*1 may be associated with a cross-section area (e.g., the width WC1*the height of the pathway 10*c*1) of the pathway 10*c*1. The diameter of the pathway 10*c*2 may be associated with a cross-section area (e.g., the width WC2*the height of the pathway 10*c*2) of the pathway 10*c*2. The cross-sectional area (e.g., the width WC1*the height of the pathway 10*c*1) of the pathway 10*c*1 may be greater than the cross-sectional area (e.g., the width WC2*the height of the pathway 10*c*2) of the pathway 10*c*2. In an alternative embodiment, the diameter of the pathway 10*c*1 is the height of the pathway 10*c*1 and the diameter of the pathway 10*c*2 is the height of the pathway 10*c*2. The height of the pathway 10*c*1 may be different from that of the pathway 10*c*2. The height of the pathway 10*c*1 may be greater than that of the pathway 10*c*2. A width of the pathway 10*c*1 may be the same as that of the pathway 10*c*2. The cross-sectional area of the pathway 10*c*1 may be greater than the cross-sectional area (e.g., the width WC2*the height of the pathway 10*c*2) of the pathway 10*c*2. In yet another alternative embodiment, the width of the pathway 10*c*1 may be different from that of the pathway 10*c*2 and the height of the pathway 10*c*1 may be different from that of the pathway 10*c*2.

Referring again to FIG. 1, a flow path of the pathway 10*c*1 that a gas flow F11 passes through may be shorter than a flow path of the pathway 10*c*2 that a gas flow F12 passes through. In brief, the flow path of the pathway 10*c*1 that the gas flow F11 passes through refers to the flow path F11 of the pathway 10*c*1, and the flow path of the pathway 10*c*2 that the gas flow F12 passes through refers to the flow path F11 of the pathway 10*c*1. In some embodiments, a flow volume passing through the pathway 10*c*1 may be greater than a flow volume passing through the pathway 10*c*2. The carrier 10 and the lid structure 14 may collectively define a compartment (or a sealed compartment) 144*e* accommodating the die 13.

Referring to FIG. 2, the carrier 10 may have a top surface 101 and a bottom surface 102 opposite to the top surface 101. The carrier 10 may include a sidewall 103, a base 104, and a circuit structure 105. The sidewall 103 may surround the base 104. The sidewall 103 may surround the top surface 101. The sidewall 103 may have a tapered lateral surface facing the die 11, 12, or 13. The sidewall 103 may be connected to the base 104 and extend from the top surface 101 in a direction perpendicular thereto. The semiconductor package 1 may include an adhesive layer 15 connecting the lid structure 14 and the sidewall 103 (e.g., a top surface of the sidewall 103). The circuit structure 105 may be disposed in the base 104 of the carrier 10. The circuit structure 105 may include a redistribution layer (RDL) including a plurality of conductive traces and/or a plurality of conductive vias.

In some embodiments, the carrier 10 may include a lead frame encapsulated by molding compounds. In some embodiments, the carrier 10 may include, for example, a printed circuit board (PCB), such as a paper-based copper foil laminate, a composite copper foil laminate, or a polymer-impregnated glass-fiber-based copper foil laminate. In some embodiments, the carrier 10 may include a semiconductor substrate including silicon, germanium, or other suitable materials.

The die 11 may be disposed over the carrier 10 (or the top surface 101 of the carrier 10). The die 11 may be electrically connected to the circuit structure 105 of the carrier 10. The die 11 may be disposed in the pathway 10*c*1. The die 11 may have a first type of application. The die 11 may include a flow sensor, which may be configured to detect a flow rate of a gas flow F11 passing through the pathway 10*c*1. The flow rate detected by the flow sensor of the die 11 may be associated with a flow rate of a gas flow that flows through a region where the semiconductor package 1 is located. In some embodiments, the flow rate detected by the flow sensor of the die 11 may be substantially the same as the flow rate of a gas flow that flows through a region where the semiconductor package 1 is located.

The die 12 may be disposed over the carrier 10 (or the top surface 101 of the carrier 10). The die 12 may be electrically connected to the circuit structure 105 of the carrier 10. The die 12 may be disposed in the pathway 10*c*2. The die 12 may have a second type of application different from the first type of application of the die 11. The die 12 may include a gas sensor or a pressure sensor. The gas sensor of the die 12 may be configured to detect a species of a gas flow F12 passing through the pathway 10*c*2. The species detected by the gas sensor of the die 12 may be associated with that of a gas flow that flows through a region where the semiconductor package 1 is located. The gas sensor of the die 12 may be configured to detect a pressure of the gas flow F12 passing through the pathway 10*c*2. The pressure detected by the pressure sensor of the die 12 may be associated with a pressure of a gas flow that flows through a region where the semiconductor package 1 is located.

The die 13 may be disposed over the carrier 10 (or the top surface 101 of the carrier 10). The die 12 may be electrically connected to circuit structure 105 of the carrier 10. The die 13 may be disposed within the sealed compartment 144*e*. The die 13 may have the same type of application as that of die 12. The die 13 may be configured to generate a reference signal for the die 12. The reference signal generated by the die 13 may be used to calibrate the die 12. The die 13 may be a differential component for the die 12.

The lid structure 14 may include a gas inlet 141, a gas outlet 142, a protrusion pattern 143, and a protrusion pattern 144. Referring to FIG. 2, the lid structure 14 may have a surface 1401 and a surface 1402 opposite to the surface 1401. The surface 1402 of the lid structure 14 may face toward the carrier 10. The protrusion pattern 143 or the protrusion pattern 144 may protrude from the surface 1402. The protrusion pattern 143 may protrude toward the carrier 10 and extend between the die 11 and the die 12. The protrusion pattern 143 may be configured to direct at least a portion of a gas flow from the gas inlet 141 into the pathway 10*c*1. The protrusion pattern 143 may be configured to direct at least a portion of a gas flow from the gas inlet 141 into the pathway 10*c*2. In some embodiments, the protrusion pattern 143 may extend into the cavity 10*a* and be configured to divide a gas flow from the gas inlet 141 into the pathway 10*c*1 and the pathway 10*c*2. In some embodiments, the protrusion pattern 143, when integrated with the carrier 10, may be configured to collectively define the pathway 10*c*1 connecting the gas inlet 141 and the gas outlet 142, and the pathway 10*c*2 diverting from the pathway 10*c*1 and connecting the gas inlet 141 and the gas outlet 142. The protrusion pattern 143 may have a line or bar shape. In some embodiments, when integrated with the carrier 10 external to the lid structure 14, the surface 1402 of the lid structure 14 and the carrier 10 may be configured to collectively define the pathway 10*c*1 and the pathway 10*c*2. The pathway 10*c*1 and the pathway 10*c*2 may both connect the gas inlet 141 and the gas outlet 142.

In some embodiments, a distance D1 between the protrusion pattern 143 and a top surface 101 of the carrier 10 may be larger than a height 11H1 of the die 11. Referring to FIG. 1, the protrusion pattern 143 may have a side 1431 and a side 1432 opposite to the side 1431. The die 11 may be disposed under the surface 1402 of the lid structure 14. The die 12 may be disposed under the surface 1402 of the lid structure 14. In some embodiments, as shown in FIG. 1, the die 11 may be disposed adjacent to the side 1431 of the protrusion pattern 143. The die 12 may be disposed adjacent to the side 1432 of the protrusion pattern 143.

Referring again to FIG. 2, protrusion pattern 144 may protrude toward the carrier 10. The protrusion pattern 144 may protrude from the surface 1402 of the lid structure 14. The protrusion pattern 144 may extend into the cavity 10*a*. The semiconductor package 1 may include an adhesive layer 151. The protrusion pattern 144 may be connected to or attached to the top surface 101 of the carrier 10 through the adhesive layer 151. The protrusion pattern 143 and the protrusion pattern 144 may be configured to collectively divide the gas flow from the gas inlet 141 at least into the pathway 10*c*1 and the pathway 10*c*2. The protrusion pattern 143 has a height 14H1 and the protrusion pattern 144 has a height 14H2. The height 14H2 may be greater than the height 14H1. In some embodiments, a sidewall (e.g., the protrusion pattern 143) of the first pathway has the height 14H1 and a second sidewall (e.g., the protrusion pattern 144) of the pathway 10*c*1 has the height 14H2 opposite to the first sidewall. The height 14H1 may be different from the height 14H2. As shown in FIG. 2, the first sidewall of the pathway 10*c*1 may be separated from the carrier with the distance D1, while the second sidewall of the pathway 10*c*1 may be separated from the carrier 10 with space in which the adhesive layer 151 is disposed. The lid structure 14 can be fastened to the carrier 10 by the adhesive layer 151 to improve the robustness of the semiconductor package 1. Furthermore, the adhesive layer 151 improves the seal of the compartment 144*e*.

A lateral space S1 between a vertical projection of the die 11 on the carrier 10 and a vertical projection of the protrusion pattern 143 on the carrier 10 is different from a lateral space S2 between a vertical projection of the die 11 on the carrier 10 and a vertical projection of the protrusion pattern 144 on the carrier 10. In some embodiments, the lateral space S1 may be smaller than the lateral space S2. Alternatively, the lateral space S1 and the lateral space S2 may be substantially the same.

Figure 3:
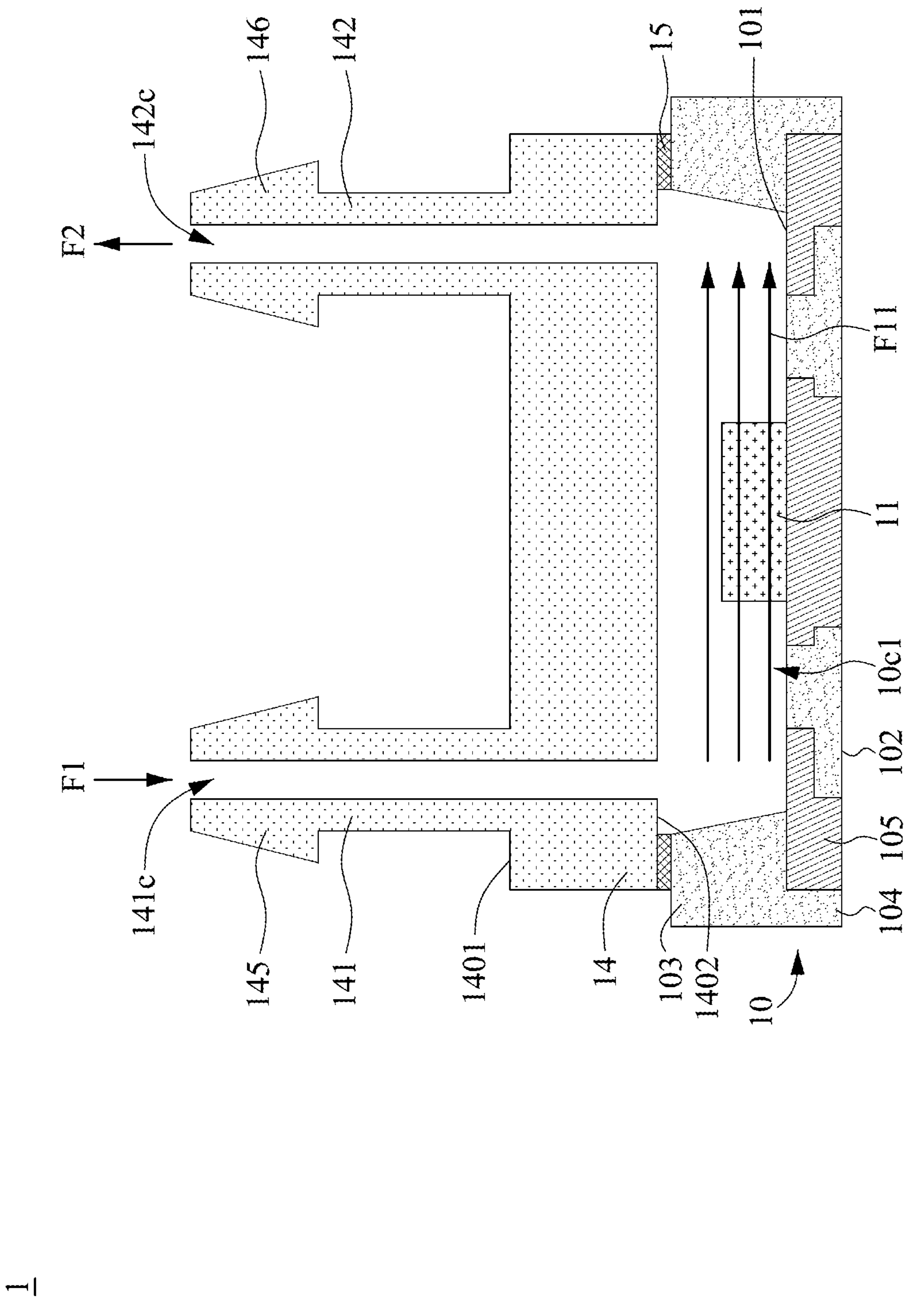
FIG. 3 is a cross-sectional view along the line B-B' in FIG. 1 in accordance with some embodiments of the present disclosure.
Figure 4:
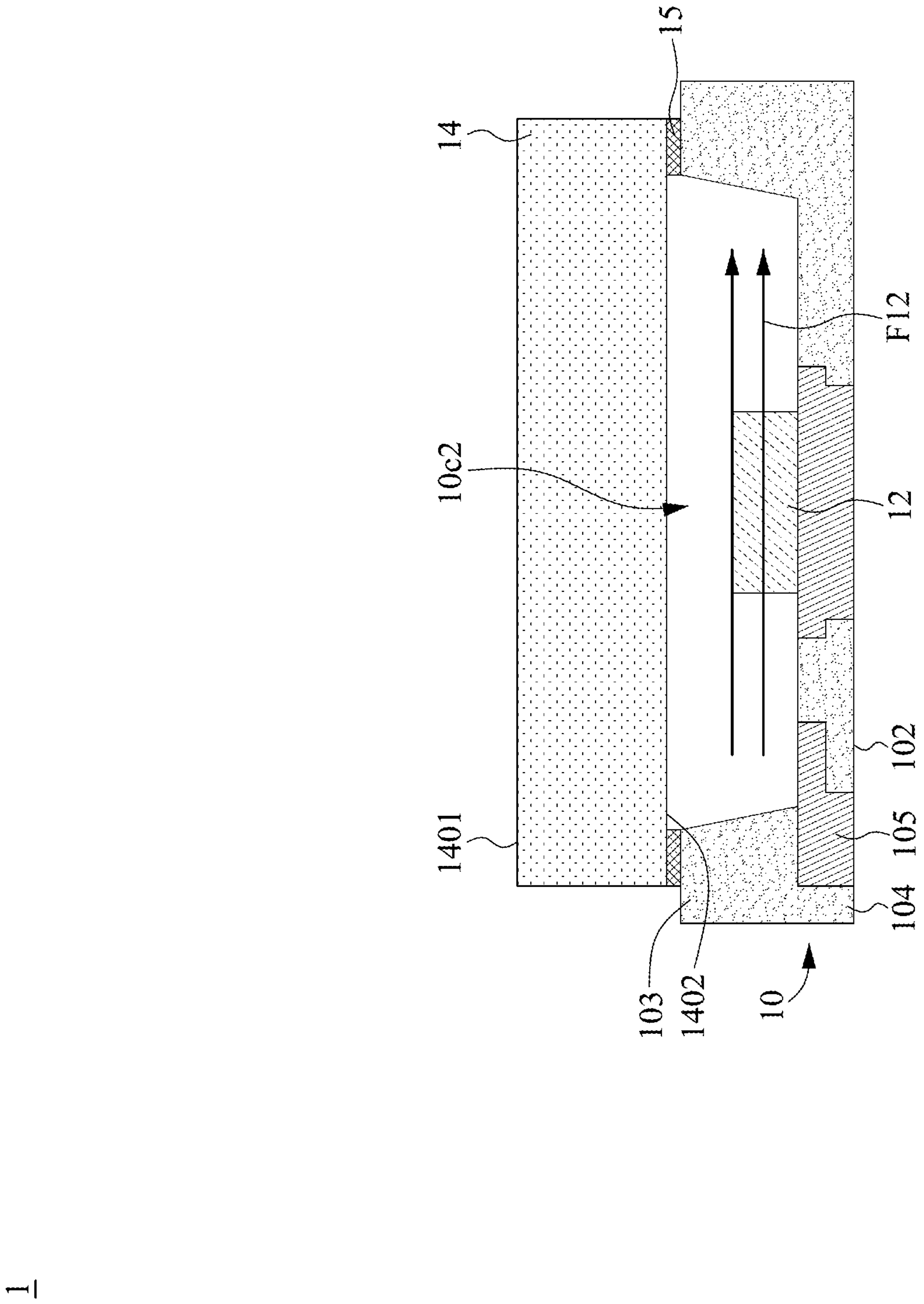
FIG. 4 is a cross-sectional view along the line C-C' in FIG. 1 in accordance with some embodiments of the present disclosure.

The gas inlet 141 and/or the gas outlet 142 may have a circular shape or a rectangular shape from a top view. The gas inlet 141 and the gas outlet 142 may be laterally aligned. FIG. 3 is a cross-sectional view along the line B-B' in FIG. 1 in accordance with some embodiments of the present disclosure. The gas inlet 141 may be spaced apart from the gas outlet 142. The gas inlet 141 and the gas outlet 142 may be arranged substantially along the same direction of the pathway 10*c*1. The gas inlet 141 and the gas outlet 142 may be arranged along a direction (e.g., line B-B') parallel to the pathway 10*c*1. The gas inlet 141 may protrude from the surface 1401 of the lid structure 14. The gas inlet 141 may have an opening vertically connecting the surface 1401 and the surface 1402 of the lid structure 14. The gas inlet 141 may be configured to allow a gas flow F1 to enter the semiconductor package 1. The gas flow F1 may be divided by the protrusion pattern 143 and/or the protrusion pattern 144 into a plurality of gas flows entering the pathway 10*c*1 or 10*c*2. As shown in FIG. 3, the gas flow F1 may be divided into the gas flow F11 that passes through the pathway 10*c*1. FIG. 4 is a cross-sectional view along the line C-C' in FIG. 1 in accordance with some embodiments of the present disclosure. As shown in FIG. 4, the gas flow F1 may be divided into the gas flow F12 that passes through the pathway 10*c*2.

The semiconductor package (or a micro electro mechanical systems (MEMS)) 1 integrates a plurality of dies 11 and 12 for different types of applications to reduce the size of the semiconductor package 1. The lid structure 14 of the semiconductor package 1 enables the detection of the plurality of dies 11 and 12 for different types of applications within the same cavity (or chamber) 10*a*. The dies 11 and 12 share the same gas inlet 141 and the same gas outlet 142 of the lid structure 14. The protrusion patterns 143 and/or 144 define the area of the pathway 10*c*1 and the pathway 10*c*2, and the flow volume and direction of a plurality of portions of the gas flow F1 from the gas inlet 141. The protrusion patterns 143 and/or 144 may divide the gas flow F1 into one gas flow (e.g., the gas flow F11) for the detection of the flow rate of the gas flow F1 and another gas flow (e.g., the gas flow F12) for the detection of the species, pressure, or other characteristics of the gas flow F1. The flow volume of the gas flow F11 and the gas flow F12 may be designed to achieve the detection of a plurality of dies for different types of applications. For example, the flow volume (or flow rate) of the gas flow F11 may be relatively high (e.g., higher than that of the gas flow F12) to precisely detect the flow rate of the gas flow F11, which is associated with the flow rate of an external gas flow passing through a region where the semiconductor package 1 is located. The flow rate of the gas flow F11 may be designed by changing the structure of the pathway C1. The flow rate of the gas flow F12 may be designed by changing the structure of the pathway C2. The design of the pathway C1 and the pathway C2 may be implemented by fluid simulation software.

Referring again to FIG. 3, the gas inlet 141 of the lid structure 14 may include a conduit 141*c* and an engaging part 145. The conduit 141*c* may connect the engaging part 145 and the lid structure 14 (or the surface 1401 of the lid structure 14). The engaging part 145 may be configured to engage with an external device, pipe, etc. The gas flow F1 may pass through the conduit 141*c*.

The gas outlet 142 may protrude from the surface 1401 of the lid structure 14. The gas outlet 142 may be configured to allow a gas flow F2 to exit the semiconductor package 1. A flow volume of the gas flow F2 may be substantially the same as that of the gas flow F1. The gas outlet 142 of the lid structure 14 may include a conduit 142*c* and an engaging part 146. The conduit 142*c* may connect the engaging part 146 and the lid structure 14 (or the surface 1401 of the lid structure 14). The engaging part 146 may be configured to engage with an external device, pipe, etc. The gas flow F2 may pass through the conduit 142*c*.

Referring again to FIG. 1, the gas inlet 141 and the gas outlet 142 may overlap opposite ends of the pathway 10*c*1 from a top view. The gas inlet 141 and the gas outlet 142 may be laterally offset from opposite ends of the pathway 10*c*2 from the top view. In some embodiments, a vertical projection of a shortest connection between the gas inlet 141 and the gas outlet 142 on the carrier 10 may not be overlapping the pathway F12 from the top view. The dislocation relationship between the gas inlet 141 and the die 12 prevents the particles in the gas flow F1 from interfering with the detection of the die 12. The influence of the particles accompanying the gas flow F1 to the pathway 10*c*2 can be alleviated. In other words, the gas flow F12 as divided from the gas flow F1 may have a relatively small numbers of particles.

Figure 5:
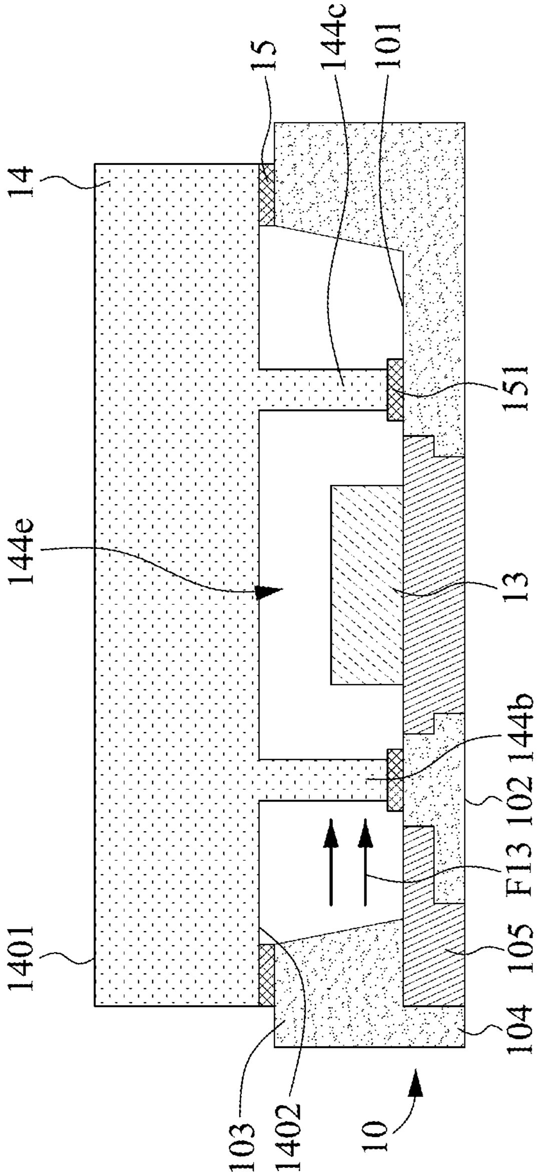
FIG. 5 is a cross-sectional view along the line D-D' in FIG. 1 in accordance with some embodiments of the present disclosure.

As shown in FIG. 1, the protrusion pattern 144 may include a primary segment 144*a*, and at least one secondary segment 144*b* and 144*c* connected to different ends of the primary segment 144*a*. The primary segment 144*a* of the protrusion pattern 144 may be parallel to the protrusion pattern 143. The at least one secondary segment 144*b* and 144*c* may be substantially perpendicular to the primary segment 144*a* of the protrusion pattern 144. The at least one secondary segment 144*b* and 144*c* may be in contact with the sidewall 103 (e.g., the tapered lateral surface of the sidewall 103) of the carrier 10. The secondary segment 144*b* of the protrusion pattern 144 may be configured to provide an obstruction to the gas flow F13. FIG. 5 is a cross-sectional view along the line D-D' in FIG. 1 in accordance with some embodiments of the present disclosure. As shown in FIG. 5, the at least one secondary segment 144*b* may be connected to the top surface 101 of the carrier 10 through the adhesive layer 151. The primary segment 144*a* and the at least one secondary segment 144*b* or 144*c*, when integrated with the carrier 10, collectively define the compartment 144*e* spatially isolated from the pathway 10*c*1 and the pathway 10*c*2. The compartment 144*e* may be a sealed compartment defined by the sidewall 103, the base 104, the protrusion pattern 144, and the surface 1402 of the lid structure 14. The die 13 disposed in the compartment 144*e* may be free from influence of the gas flow F1. The compartment 144*e* may be configured to provide a stable, enclosed space to the die 13. As shown in FIG. 5, the gas flow F13 as divided from the gas flow F1 is unable to enter the compartment 144*e*. The die 13 may be configured to generate a reference signal for calibrating the detection of the die 12. The accuracy of the detection of the species can be improved.

Figure 6:
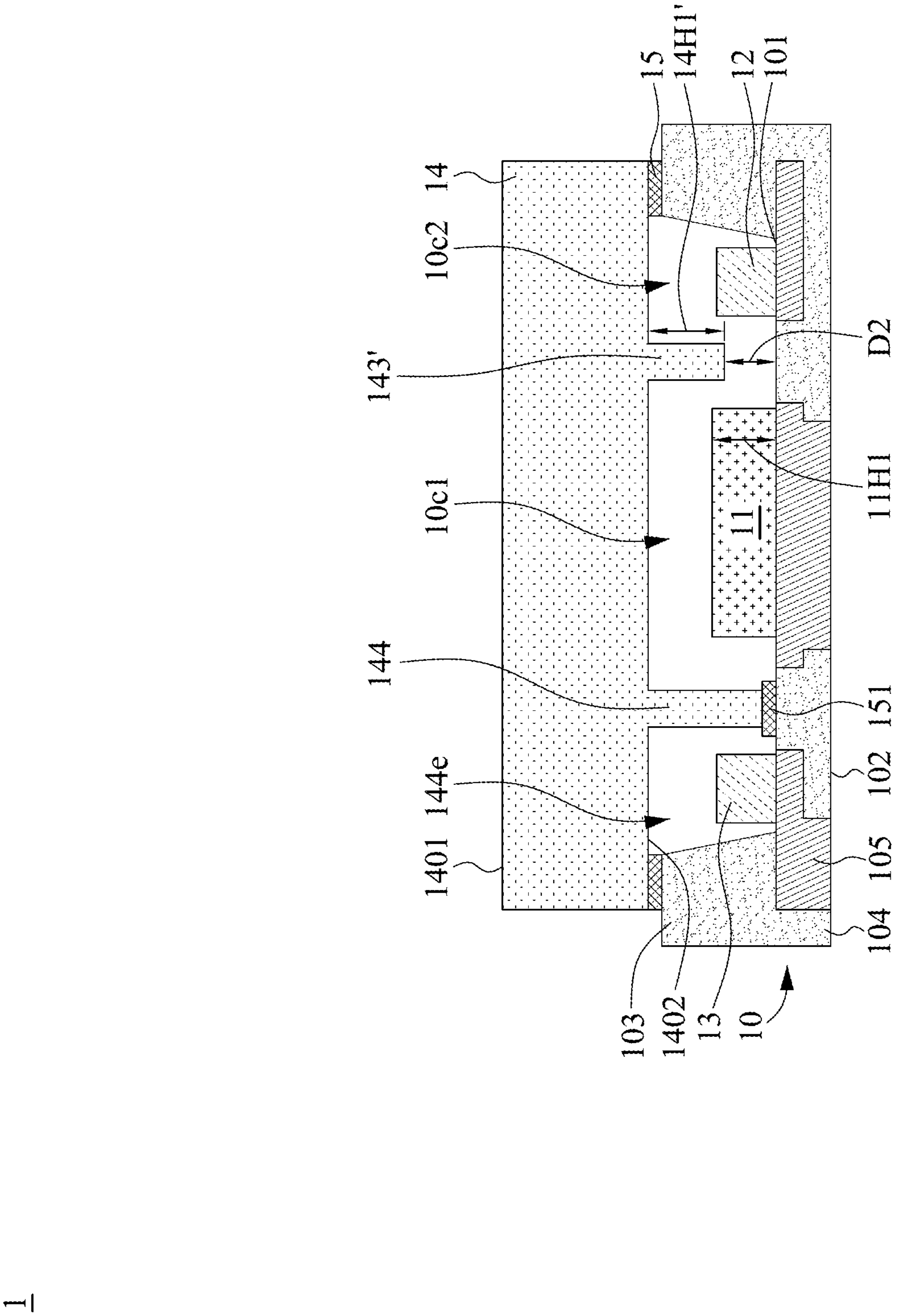
FIG. 6 is another cross-sectional view along the line A-A' in FIG. 1 in accordance with some embodiments of the present disclosure.

FIG. 6 is another cross-sectional view along the line A-A' in FIG. 1 in accordance with some embodiments of the present disclosure. Some detailed descriptions may correspond to preceding paragraphs related to FIG. 2 and are not repeated hereinafter for conciseness, with differences therebetween as follows. As shown in FIG. 6, a protrusion pattern 143' may be similar to the protrusion pattern 143 of FIG. 2 except that the protrusion pattern 143' may have a height 14H1' greater than the 14H1 of the protrusion pattern 143. A distance D2 between a protrusion pattern 143' and the top surface 101 of the carrier 10 may be shorter than the height 11H1 of the die 11. In some embodiments, a bottom surface of the protrusion pattern 143 (or the first sidewall of the pathway 10*c*1) may be at a lower elevation than a top surface of the die 11.

Figure 7:
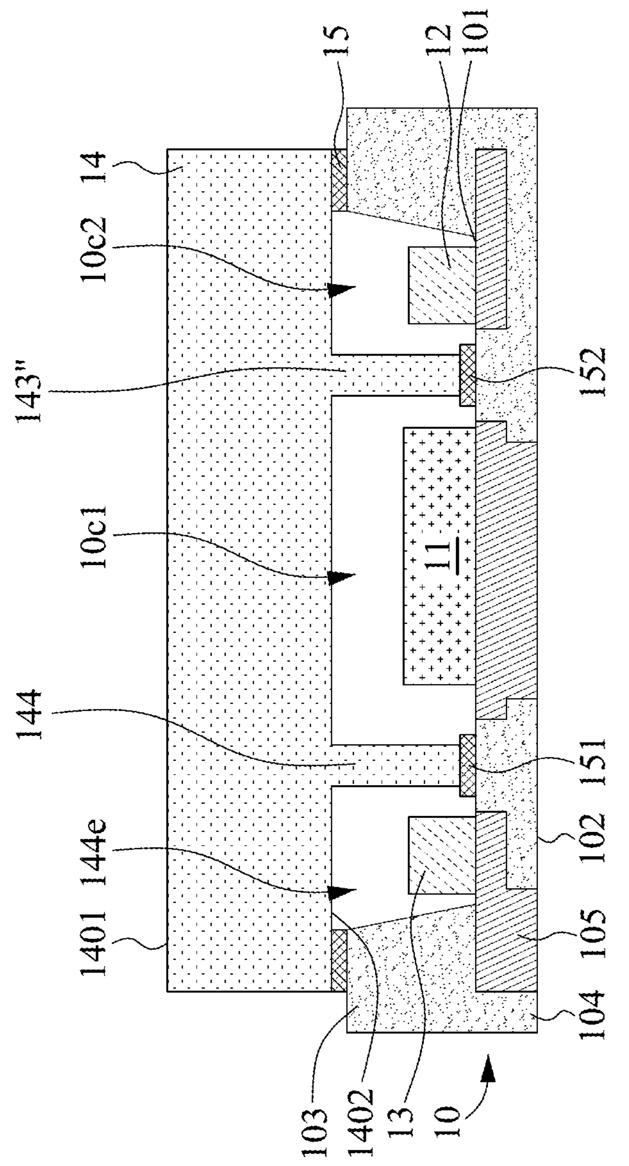
FIG. 7 is another cross-sectional view along the line A-A' in FIG. 1 in accordance with some embodiments of the present disclosure.

FIG. 7 is another cross-sectional view along the line A-A' in FIG. 1 in accordance with some embodiments of the present disclosure. Some detailed descriptions may correspond to preceding paragraphs related to FIG. 2 and are not repeated hereinafter for conciseness, with differences therebetween as follows. As shown in FIG. 7, a protrusion pattern 143" may be similar to the protrusion pattern 143 of FIG. 2 except that the protrusion pattern 143" is attached to the top surface 101 of the carrier 10 through an adhesive layer 152. In some embodiments, the adhesive layer 151/152 may be disposed at least in one of a space between the protrusion pattern 143 (or the first sidewall of the pathway 10*c*1) and the carrier or a space between the protrusion pattern 144 (or the second sidewall of the pathway 10*c*1) and the carrier.

By the adjustment of the height of the protrusion pattern (e.g., the protrusion patterns 143, 143', and 143"), the flow volume or the flow rate of the gas flows F11 and F12 may be adjusted depending on the requirement of the detection conditions of the dies 11 and 12.

Figure 8:
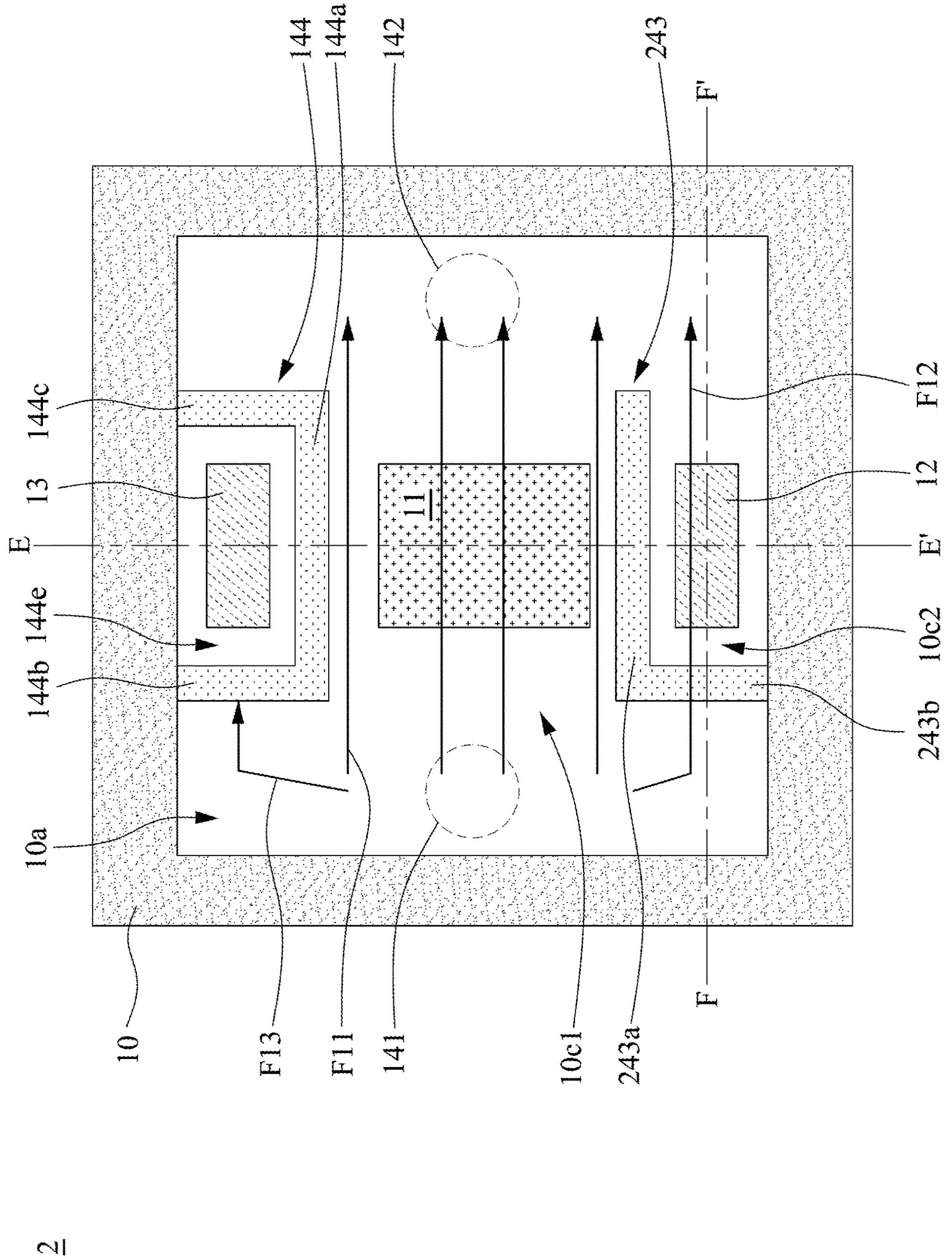
FIG. 8 is a perspective view of a semiconductor package in accordance with some embodiments of the present disclosure.

FIG. 8 is a perspective view of a semiconductor package 2 in accordance with some embodiments of the present disclosure. The semiconductor package 2 in FIG. 8 is similar to the semiconductor package 1 in FIG. 1. Therefore, some detailed descriptions may correspond to preceding paragraphs and are not repeated hereinafter for conciseness, with differences therebetween as follows.

As shown in FIG. 8, the lid structure 14 of the semiconductor package 2 includes a protrusion pattern 243. The protrusion pattern 243 may include a primary segment 243*a* and a secondary segment 243*b*. The primary segment 243*a* of the protrusion pattern 243 of the semiconductor package 2 may be similar to the protrusion pattern 143. The secondary segment 243*b* may be substantially perpendicular to the primary segment 243*a* of the protrusion pattern 243. The secondary segment 243*b* of the protrusion pattern 243 may be closer to the gas inlet 141 than to the gas outlet 142. The at least one secondary segment 243*b* may be in contact with the sidewall 103 (e.g., the tapered lateral surface of the sidewall 103) of the carrier 10. In some embodiments, the protrusion pattern 243 may have an L shape.

Figure 9:
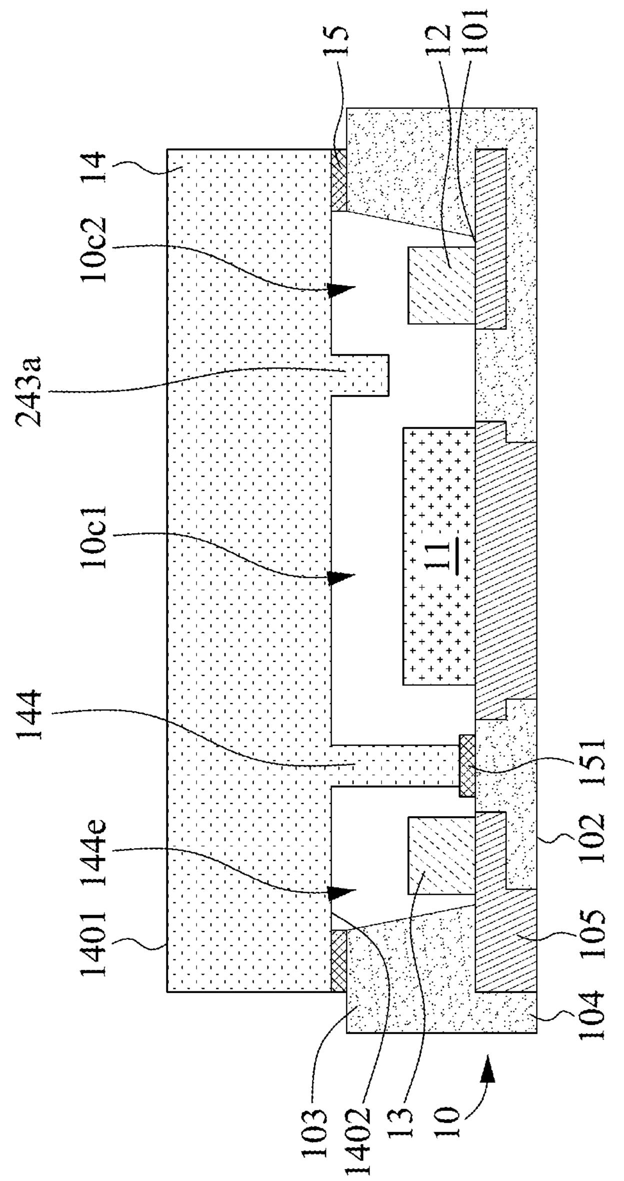
FIG. 9 is a cross-sectional view along the line E-E' in FIG. 8 in accordance with some embodiments of the present disclosure.
Figure 10:
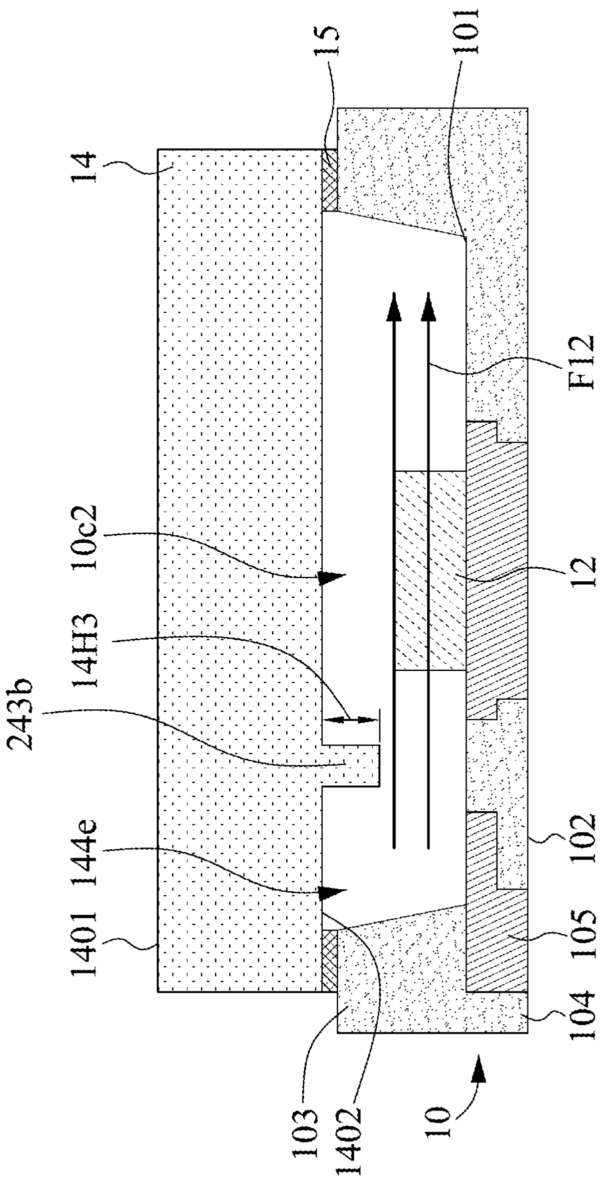
FIG. 10 is a cross-sectional view along the line F-F' in FIG. 8 in accordance with some embodiments of the present disclosure.

FIG. 9 is a cross-sectional view along the line E-E' in FIG. 8 in accordance with some embodiments of the present disclosure. The primary segment 243*a* of the protrusion pattern 243 may be similar to the protrusion pattern 143 in FIG. 2. In some embodiments, the primary segment 243*a* of the protrusion pattern 243 may be similar to the protrusion pattern 143' in FIG. 6 and the protrusion pattern 143" in FIG. 7. FIG. 10 is a cross-sectional view along the line F-F' in FIG. 8 in accordance with some embodiments of the present disclosure. The secondary segment 243*b* may protrude from the surface 1402 of the lid structure 14. The secondary segment 243*b* may have a height 14H3. The height 14H3 of the secondary segment 243*b* may be the same as or different from that of the primary segment 243*a* of the protrusion pattern 243. The height 14H3 may be smaller than that of the primary segment 243*a* (or the height 14H1 of the protrusion pattern 143 in FIG. 2). The secondary segment 243*b* may be configured to adjust the flow amount of the gas flow F12 entering the pathway 10*c*2. In some embodiments, the height 14H3 of the secondary segment 243*b* may vary to adjust the amount of the gas flow F12 entering the pathway 10*c*2. In some embodiments, the secondary segment 243*b* may be configured to provide an obstruction to the gas flow F12. In some embodiments, the secondary segment 243*b* may be attached to the top surface 101 of the carrier 10 through an adhesive layer.

Figure 11:
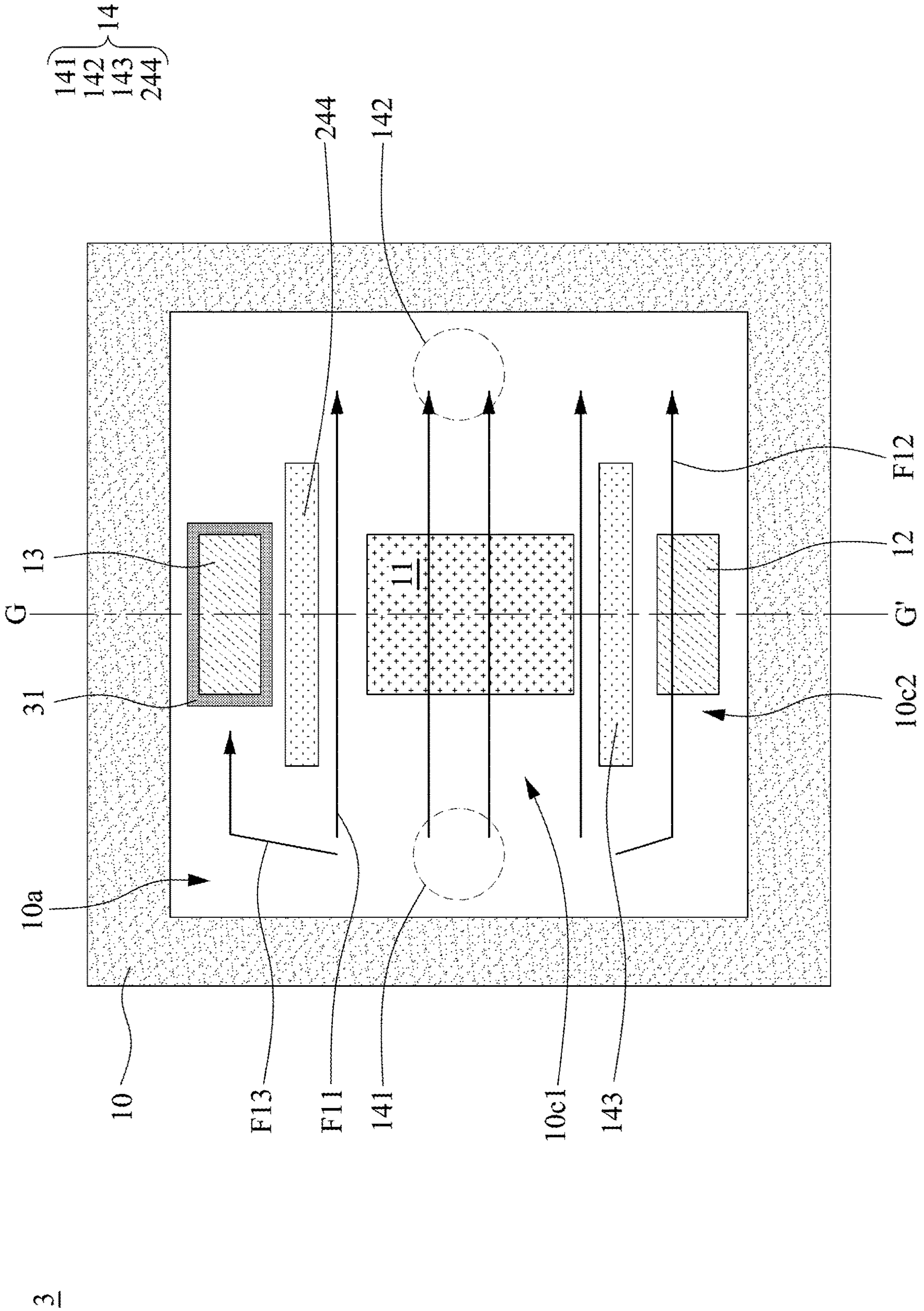
FIG. 11 is a perspective view of a semiconductor package in accordance with some embodiments of the present disclosure.

FIG. 11 is a perspective view of a semiconductor package 3 in accordance with some embodiments of the present disclosure. The semiconductor package 3 in FIG. 11 is similar to the semiconductor package 1 in FIG. 1. Therefore, some detailed descriptions may correspond to preceding paragraphs and are not repeated hereinafter for conciseness, with differences therebetween as follows.

The die 13 may be covered by a protection layer 31. The die 13 may be free from influence of the gas flow F13. As shown in FIG. 5, the gas flow F13 may be unable to enter the protection layer 31. The die 13 may be configured to generate a reference signal for calibrating the detection of the die 12. The accuracy of the detection of the species can be improved.

In some embodiments, the protection layer 31 may include an encapsulant, such as an epoxy resin, a molding compound (e.g., an epoxy molding compound or other molding compound), a polyimide, a phenolic compound or material, a material including a silicone dispersed therein, or a combination thereof.

Figure 12:
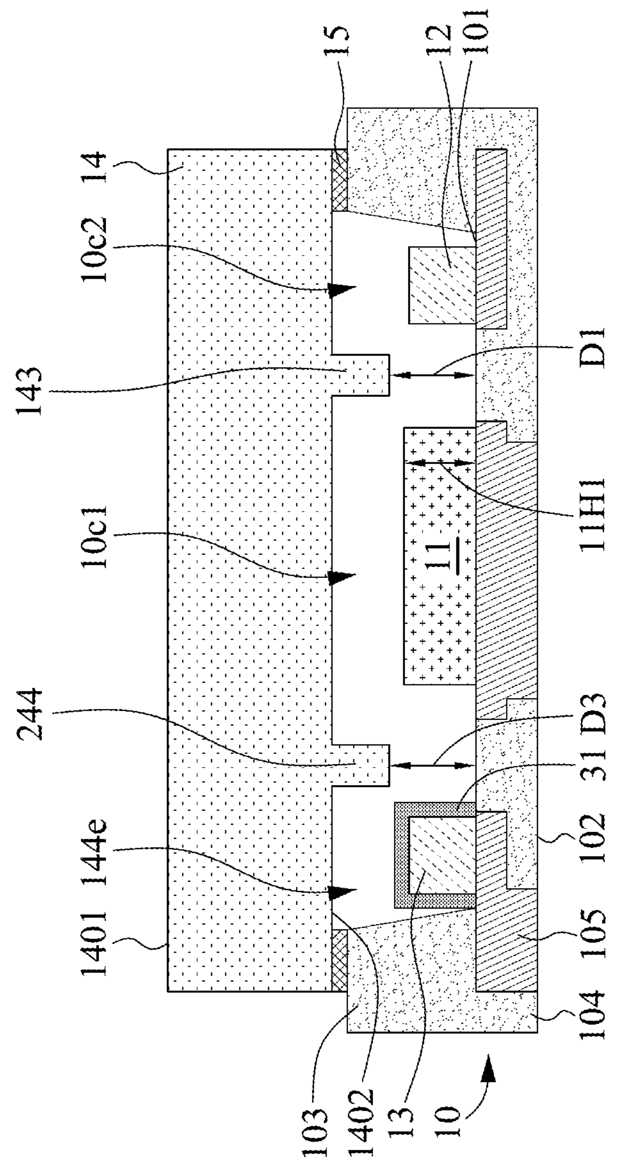
FIG. 12 is a cross-sectional view along the line G-G' in FIG. 11 in accordance with some embodiments of the present disclosure.

FIG. 12 is a cross-sectional view along the line G-G' in FIG. 11 in accordance with some embodiments of the present disclosure. The lid structure 14 may include a protrusion pattern 244 similar to the protrusion pattern 143 in FIG. 1. In some embodiments, the protrusion pattern 143 and the protrusion pattern 244 may be symmetrical. A distance D3 between the protrusion pattern 244 and the top surface 101 of the carrier 10 may be substantially the same as the height D1. In some embodiments, the height D3 may be different from the height D1. In some embodiments, the protrusion pattern 244 may be similar to the primary segment 144*a* of the protrusion pattern 144 in FIG. 1.

Figure 13:
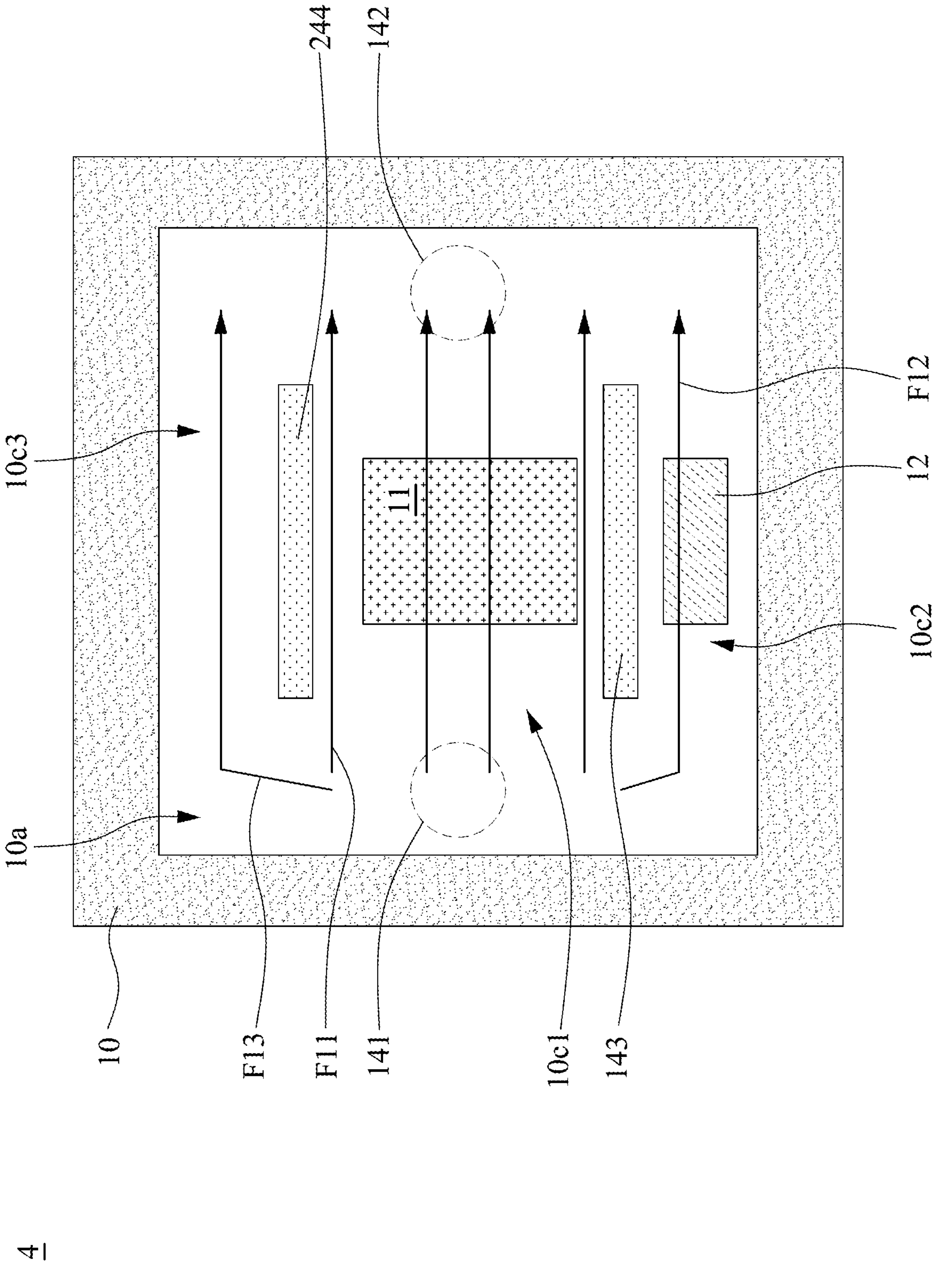
FIG. 13 is a perspective view of a semiconductor package in accordance with some embodiments of the present disclosure.

FIG. 13 is a perspective view of a semiconductor package 4 in accordance with some embodiments of the present disclosure. The semiconductor package 4 in FIG. 12 is similar to the semiconductor package 3 in FIG. 11. Therefore, some detailed descriptions may correspond to preceding paragraphs and are not repeated hereinafter for conciseness, with differences therebetween as follows.

The semiconductor package 4 may not include the die 13 of the semiconductor package 1. The protrusion pattern 244, when integrated with the carrier 10, may be configured to collectively define a pathway 10*c*3 connecting the gas inlet 141 and the gas outlet 142. The gas flow F13 may pass through the pathway 10*c*3.

Figure 14:
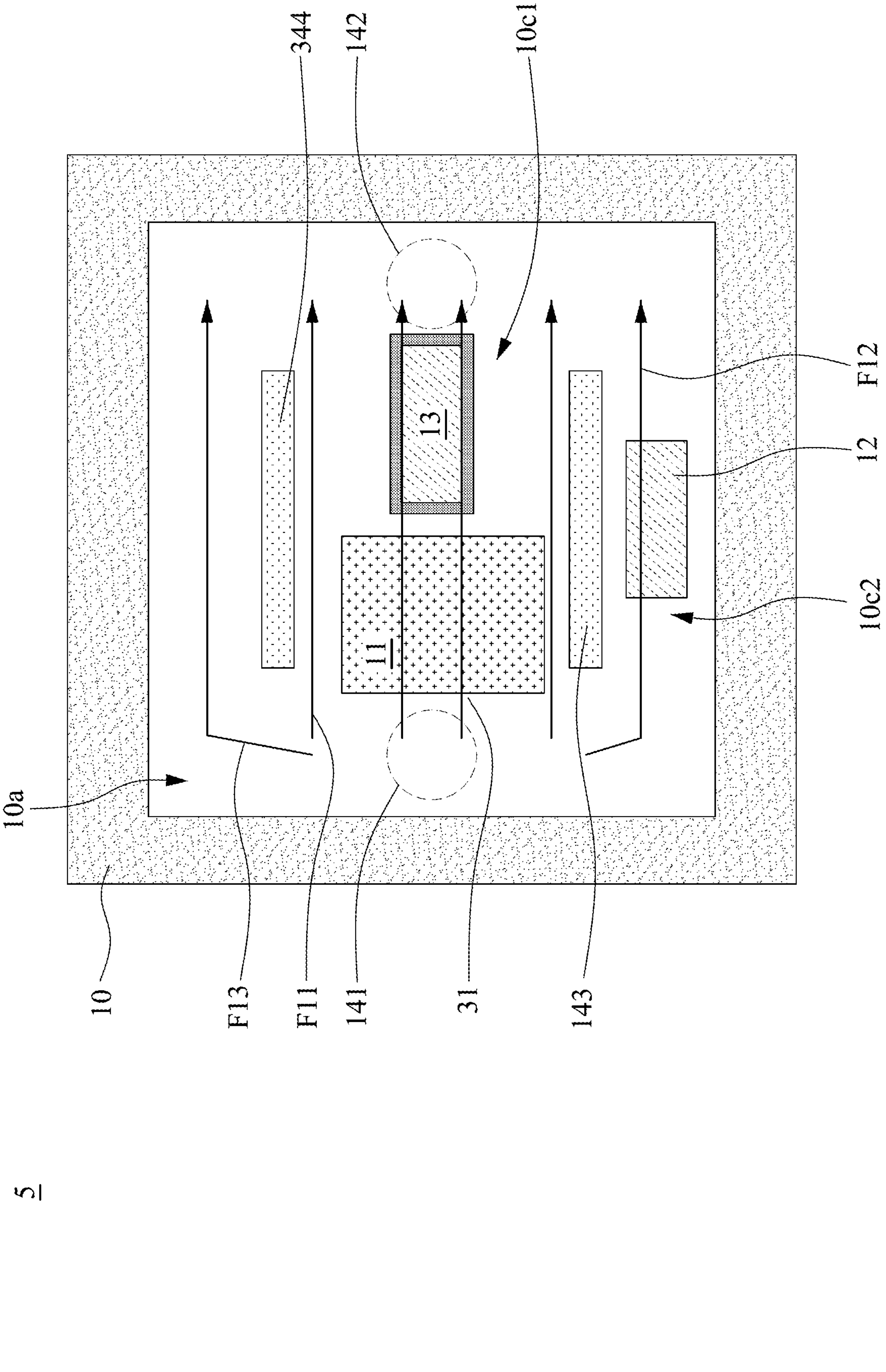
FIG. 14 is a cross-sectional view of a semiconductor package in accordance with some embodiments of the present disclosure.

FIG. 14 is a perspective view of a semiconductor package 5 in accordance with some embodiments of the present disclosure. The semiconductor package 5 in FIG. 14 is similar to the semiconductor package 3 in FIG. 11. Therefore, some detailed descriptions may correspond to preceding paragraphs and are not repeated hereinafter for conciseness, with differences therebetween as follows.

The die 13 with the protection layer 31 may be disposed in the pathway 10*c*1. The die 11 may be disposed adjacent to the gas inlet 141 and the die 13 may be disposed adjacent to the gas outlet 142. In an alternative embodiment, the die 13 may be disposed adjacent to the gas inlet 141 and the die 11 may be disposed adjacent to the gas outlet 142. In such an arrangement, the die 13 may change the flow amount or flow rate of the gas flow F11.

Figure 15:
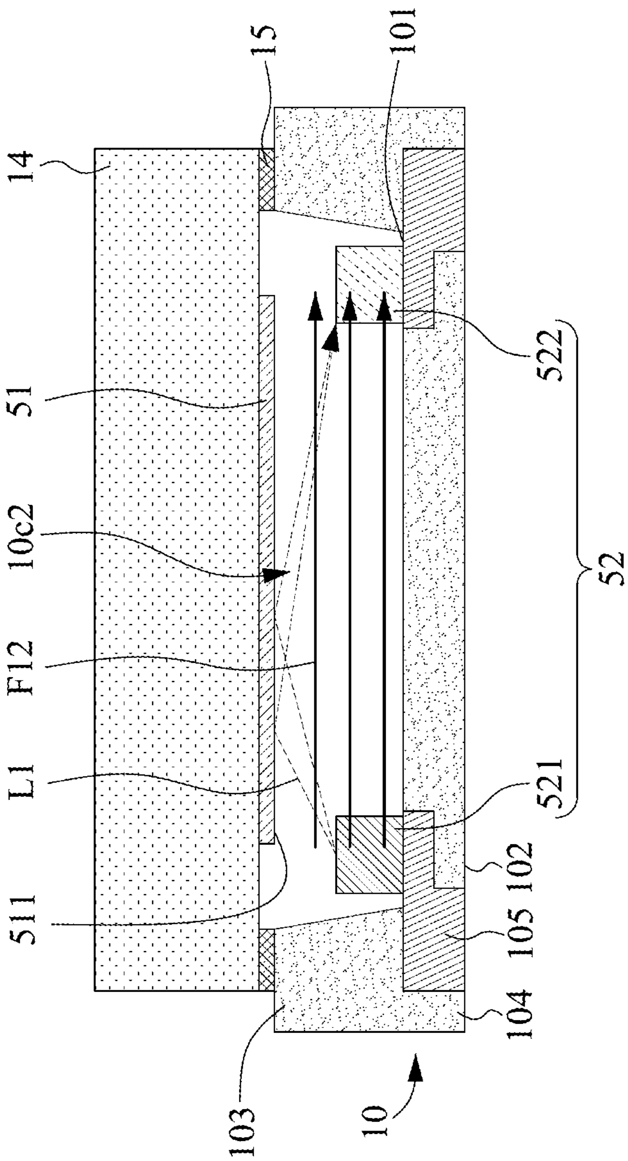
FIG. 15 is a cross-sectional view of a semiconductor package in accordance with some embodiments of the present disclosure.

FIG. 15 is a cross-sectional view of a semiconductor package 6 in accordance with some embodiments of the present disclosure. The semiconductor package 6 in FIG. 15 is similar to the semiconductor package 1 in FIG. 4. Therefore, some detailed descriptions may correspond to preceding paragraphs and are not repeated hereinafter for conciseness, with differences therebetween as follows.

The semiconductor package 6 may include a die set (or a die) 52 disposed in the pathway 10*c*2. The die set 52 may include a gas sensor or a pressure sensor. The die set 52 may be disposed above the carrier 10. The die set 52 may include an emitter 521 configured to emit an optical signal L1 and a receiver 522 configured to receive the optical signal L1. The emitter 521 may be electrically connected to the circuit structure 105 of the carrier 10. The receiver 522 may be electrically connected to the circuit structure 105 of the carrier 10. The emitter 521 and the receiver 522 may be disposed along a direction parallel to a travelling direction of the gas flow F12. The die set 52 may be configured to detect the species of the gas flow F12. The optical signal L1 emitted by the emitter L1 may interact with the species of the gas flow F12. For example, the species of the gas flow F12 may scatter the optical signal L1. As such, the spectrum, intensity, spatial distribution, or other characteristics of the optical signal L1 may be altered depending on the species of the gas flow F12. The receiver 522 may receive the altered optical signal L1. The receiver 522 may have a processing circuit to determine the species of the gas flow F12 based on the altered optical signal L1. In some embodiments, the receiver 522 may be configured to convert the altered optical signal L1 to an electrical signal or another optical signal. Subsequently, the electrical signal (or the other optical signal) may be transmitted from the receiver 522 to a circuit (not shown) in the semiconductor package 1 or an external circuit to determine the species of the gas flow F12.

As shown in FIG. 15, the semiconductor package 6 may include a reflector 51 disposed at the surface 1402 of the lid structure 14 and exposed to the pathway 10*c*2. The reflector 51 may be disposed in the optical path of the optical signal L1 and wavelength-specific to the optical signal L1. The reflector 51 may extend along the surface 1402 of the lid structure 14. The reflector 51 may be disposed above the die set 52. The reflector 51 may overlap the die set 52. The reflector 51 may include a metal material for reflecting the optical signal L1. In some embodiments, the optical signal L1 may have a total internal reflection at a bottom surface 511 of the reflector 51. The reflector 51 may be configured to provide an optical path of the optical signal L1 between the emitter 521 and the receiver 522. As such, the optical signal L1 may have more chances to interact with the species of the gas flow F12, and the variation of the spectrum, intensity, spatial distribution, or other characteristics of the altered optical signal L1 may be increased or enhanced. The die set 52 may have a higher resolution regarding the species of the gas flow F12 and the amount thereof. Furthermore, the reflector 51 is used for enhancing the detection accuracy of the gas concentration. The detected gas concentration and the optical signal L1 may be correlated by implementing algorithm.

Figure 16:
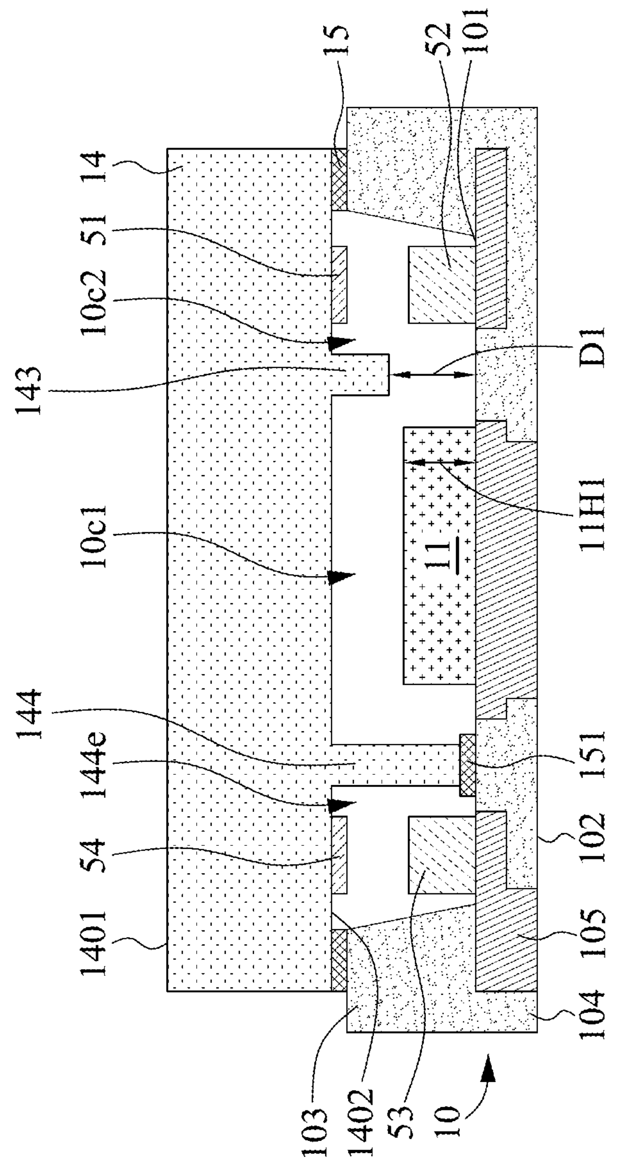
FIG. 16 is a perspective view of a semiconductor package in accordance with some embodiments of the present disclosure.

FIG. 16 is a cross-sectional view of the semiconductor package 6 in accordance with some embodiments of the present disclosure. The semiconductor package 6 in FIG. 16 is similar to the semiconductor package 1 in FIG. 2. Therefore, some detailed descriptions may correspond to preceding paragraphs and are not repeated hereinafter for conciseness, with differences therebetween as follows.

The semiconductor package 6 may include a die set 53 disposed in the compartment 144*e*. The die set 53 may be disposed above the carrier 10. The die set 53 may be similar to the die set 52. The semiconductor package 6 may include a reflector 54 disposed at the surface 1402 of the lid structure 14. The reflector 54 may overlap the die set 53. The reflector 54 may be similar to the reflector 51. The reflector 54 may be configured to increase the optical path of an optical signal emitted by an emitter of the die set 53. The die set 53 and the reflector 54 disposed in the compartment 144*e* may be free from influence of the gas flow F1. The die set 53 may be configured to generate a reference signal for calibrating the detection of the die set 52. The die set 53 is a differential component for the die set 52. The accuracy of the detection of the species can be improved.

Figure 17:
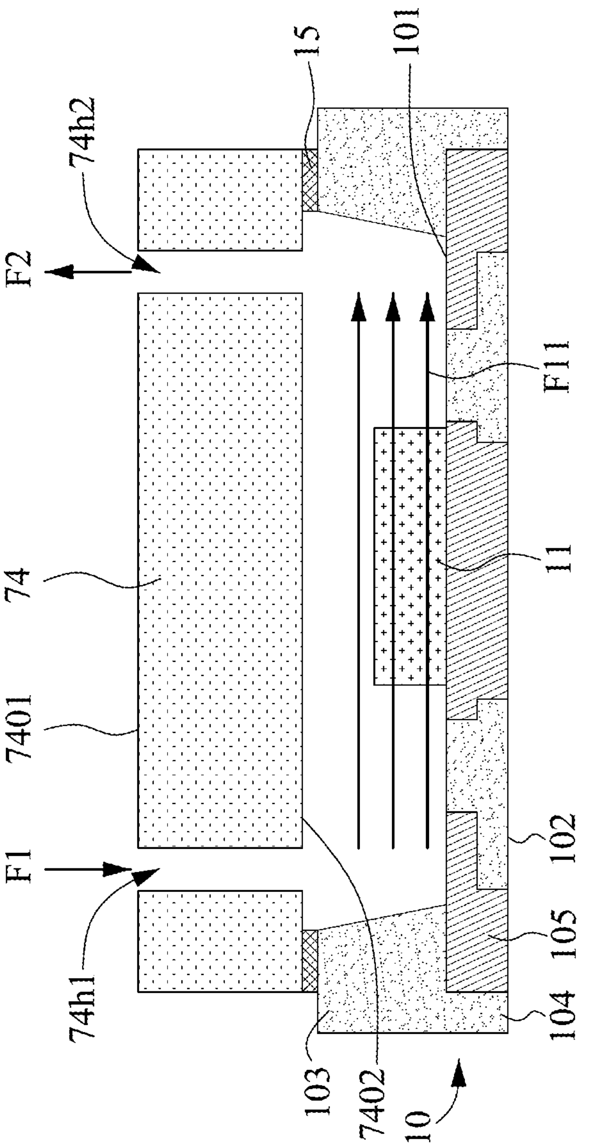
FIG. 17 is a cross-sectional view of a semiconductor package in accordance with some embodiments of the present disclosure.

FIG. 17 is a cross-sectional view of a semiconductor package 7 in accordance with some embodiments of the present disclosure. The semiconductor package 7 in FIG. 17 is similar to the semiconductor package 1 in FIG. 3. Therefore, some detailed descriptions may correspond to preceding paragraphs and are not repeated hereinafter for conciseness, with differences therebetween as follows.

The semiconductor package 7 may include a lid structure 74 instead of the lid structure 14 of the semiconductor package 1. The lid structure 74 may have a surface 7401 and a surface 7402 opposite to the surface 7401. The surface 7402 may face toward the carrier 10. The lid structure 74 may define a gas inlet (or a hole) 74*h*1 and a gas outlet (or a hole) 74*h*2. The gas inlet 74*h*1 may not protrude from the surface 7401 of the lid structure 74. The gas inlet 74*h*1 may allow the gas flow F1 to enter the semiconductor package 7. The gas outlet 74*h*2 may allow the gas flow F2 to exit the semiconductor package 7. In some embodiments, the lid structure 74 may include a plurality of protrusion patterns similar to those of the lid structure 14 (e.g., the protrusion pattern 143 or 144). The flow rate detected by the flow sensor of the die 11 may be substantially the same as the flow rate of a gas flow that flows through a region where the semiconductor package 7 is located. In an alternative embodiment, the flow rate detected by the flow sensor of the die 11 may be different from the flow rate of a gas flow that flows through a region where the semiconductor package 7 is located. The difference of the flow rate can be acquired by fluid simulation software.

Figure 18:
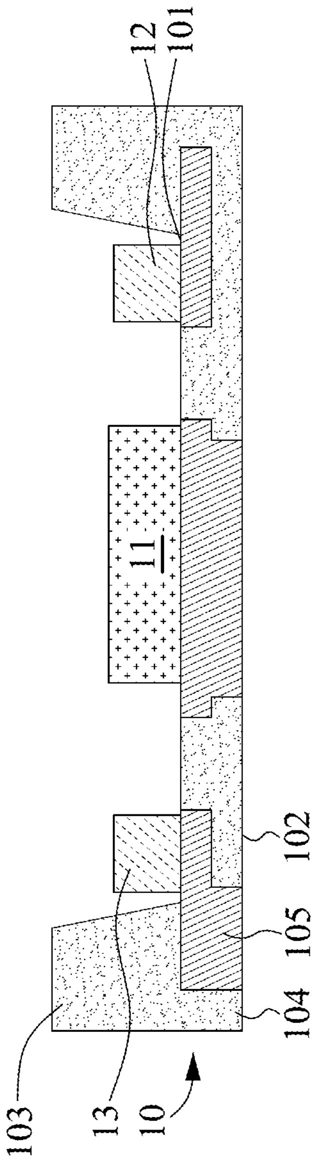
FIG. 18 shows one or more stages of an exemplary method for manufacturing a semiconductor package according to some embodiments of the present disclosure.

FIG. 18 shows one or more stages of an exemplary method for manufacturing a semiconductor package (e.g., the semiconductor package 1, 2, 3, 4, 5, 6, and 7) according to some embodiments of the present disclosure.

As shown in FIG. 18, a carrier 10 may be provided. The carrier 10 may have a surface 101 and a surface 102 opposite to the surface 101. The carrier 10 may include a sidewall 103, a base 104, and a circuit structure 105. The sidewall 103 may be connected to the base 104. The circuit structure 105 may be disposed in the base 104. Furthermore, a die 11 may be attached to the surface 101 of the carrier 10. A die 12 may be attached to the surface 101 of the carrier 10. A die 13 may be attached to the surface 101 of the carrier 10. The die 11 may be disposed between the die 12 and the die 13. The die 11 may have a first type of application. The die 12 may have a second type of application different from the first type of application. The die 13 may have the same type of application as that of the die 12.

Figure 19:
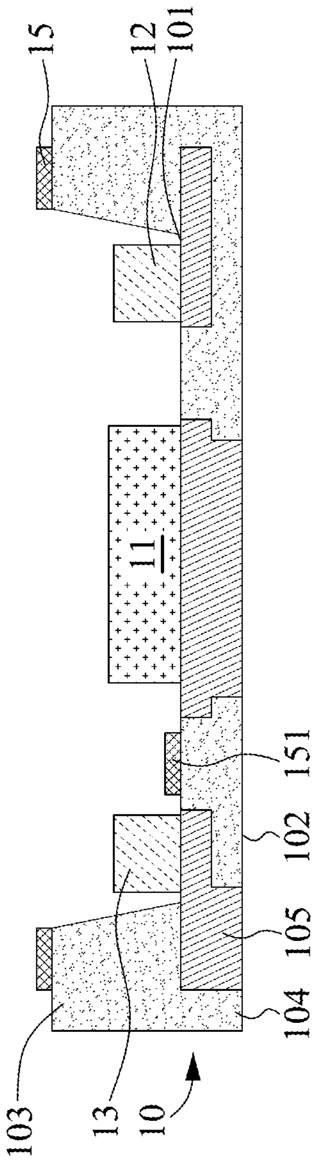
FIG. 19 shows one or more stages of an exemplary method for manufacturing a semiconductor package according to some embodiments of the present disclosure.

FIG. 19 shows one or more stages of an exemplary method for manufacturing a semiconductor package (e.g., the semiconductor package 1, 2, 3, 4, 5, 6, and 7) according to some embodiments of the present disclosure.

As shown in FIG. 19, an adhesive layer 15 is formed on the sidewall 103 of the carrier 10 and an adhesive layer 151 is formed on the surface 101 of the carrier 10. The adhesive layer 151 is formed between the die 11 and the die 13.

Figure 20:
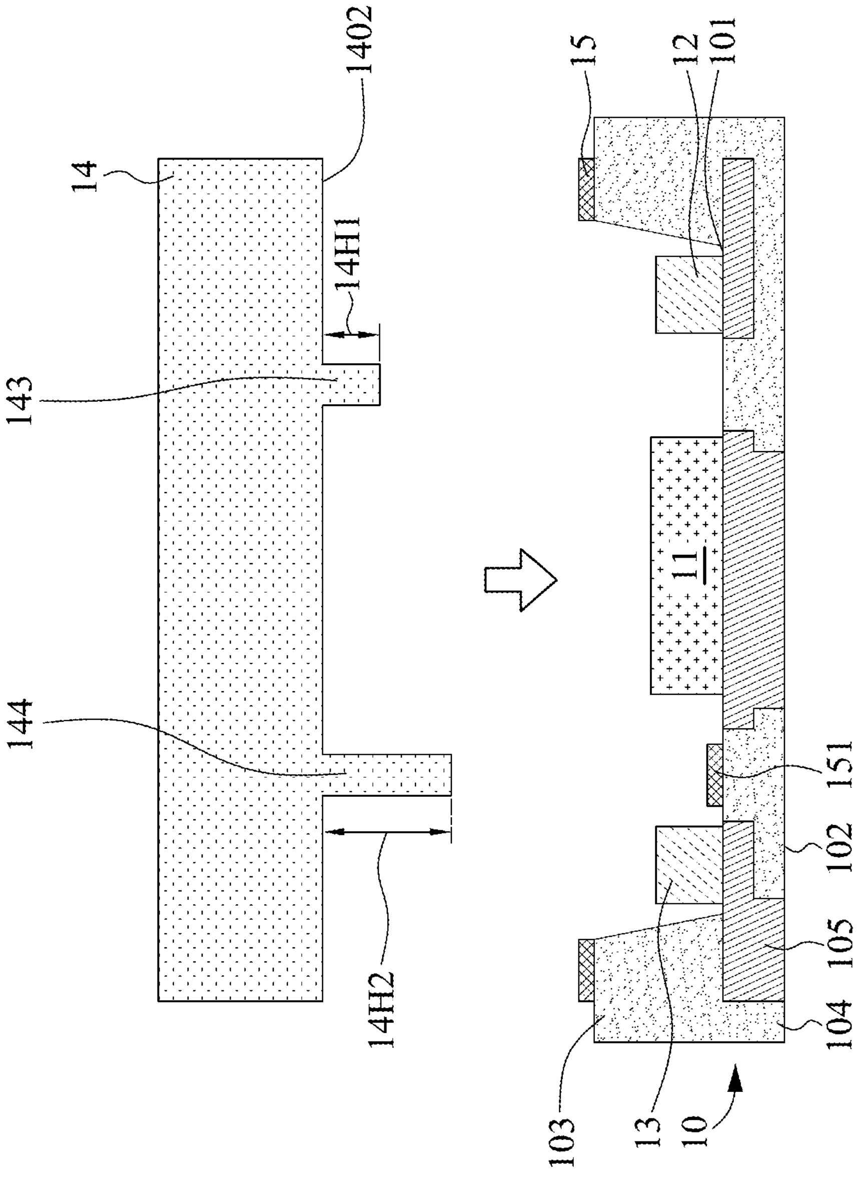
FIG. 20 shows one or more stages of an exemplary method for manufacturing a semiconductor package according to some embodiments of the present disclosure.

FIG. 20 shows one or more stages of an exemplary method for manufacturing a semiconductor package (e.g., the semiconductor package 1, 2, 3, 4, 5, and 6) according to some embodiments of the present disclosure.

As shown in FIG. 20, a lid structure 14 may be attached to the carrier 10. The lid structure may be attached to the sidewall 103 of the carrier 10 through the adhesive layer 15. The lid structure 14 may include a protrusion pattern 143 protruding from a surface 1402 of the lid structure 14 and a protrusion pattern 144 protruding from a surface 1402 of the lid structure 14. The protrusion pattern 143 may have a height 14H1 and the protrusion pattern 144 may have a height 14H2. The height 14H2 of the protrusion pattern 144 may be different from the height 14H1 of the protrusion pattern 143. The height 14H2 may be greater than the height 14H1. The protrusion pattern 144 may be attached to the surface 101 of the carrier 10 through the adhesive layer 151. The protrusion pattern 143 may be disposed between the die 11 and the die 13.

Figure 21:
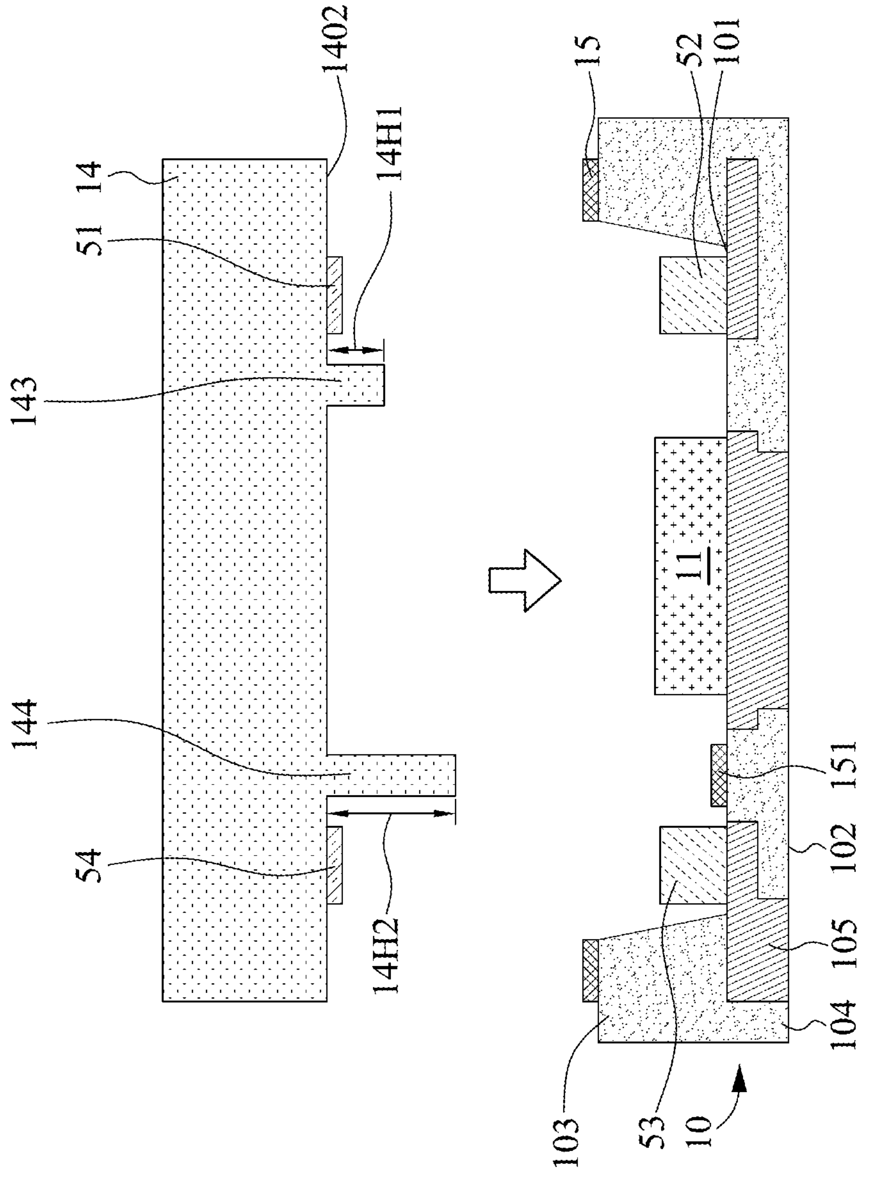
FIG. 21 shows one or more stages of an exemplary method for manufacturing a semiconductor package according to some embodiments of the present disclosure.

FIG. 21 shows one or more stages of an exemplary method for manufacturing a semiconductor package (e.g., the semiconductor package 6) according to some embodiments of the present disclosure. Similar to the FIG. 20, the lid structure 14 may be attached to the carrier 10. Prior to attaching the lid structure 14 to the carrier 10, a reflector 51 and a reflector 54 may be formed on a surface 1402 of the lid structure 14. A die set 52, instead of the die 11, may be disposed over the surface 101 of the carrier 10. A die set 53, instead of the die 13, may be disposed over the surface 101 of the carrier 10. The reflector 51 may be substantially aligned with the die set 52. The reflector 54 may be substantially aligned with the die set 53.

Spatial descriptions, such as “above,” “below,” “up,” “left,” “right,” “down,” “top,” “bottom,” “vertical,” “horizontal,” “side,” “higher,” “lower,” “upper,” “over,” “under,” and so forth, are indicated with respect to the orientation shown in the figures unless otherwise specified. It should be understood that the spatial descriptions used herein are for purposes of illustration only, and that practical implementations of the structures described herein can be spatially arranged in any orientation or manner, provided that the merits of embodiments of this disclosure are not deviated from by such an arrangement.

As used herein, the terms “approximately,” “substantially,” “substantial” and “about” are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be “substantially” the same or equal if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Two surfaces can be deemed to be coplanar or substantially coplanar if a displacement between the two surfaces is no greater than 5 μm, no greater than 2 μm, no greater than 1 μm, or no greater than 0.5 μm.

As used herein, the singular terms “a,” “an,” and “the” may include plural referents unless the context clearly dictates otherwise.

As used herein, the terms “conductive,” “electrically conductive” and “electrical conductivity” refer to an ability to transport an electric current. Electrically conductive materials typically indicate those materials that exhibit little or no opposition to the flow of an electric current. One measure of electrical conductivity is Siemens per meter (S/m). Typically, an electrically conductive material is one having a conductivity greater than approximately $10^4$ S/m, such as at least $10^5$ S/m or at least $10^6$ S/m. The electrical conductivity of a material can sometimes vary with temperature. Unless otherwise specified, the electrical conductivity of a material is measured at room temperature.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. A semiconductor package, comprising:

a carrier;

a lid structure disposed over the carrier, the lid structure including a gas inlet and a gas outlet;

a first die disposed over the carrier; and a second die disposed over the carrier, wherein the lid structure includes a first protrusion pattern protruding toward the carrier and extending between the first die and the second die, wherein the lid structure and the carrier collectively define a first pathway and a second pathway to respectively accommodate the first die and the second die, wherein the lid structure and the carrier collectively define a sealed compartment accommodating a third die, and wherein the lid structure further comprises a second protrusion pattern defining the sealed compartment, and wherein the first die is disposed between the first protrusion pattern and the second protrusion pattern.

2. The semiconductor package of claim 1, wherein the second die is a die set comprising an emitter and a receiver, the emitter being configured to emit a first optical signal, and the receiver being configured to receive the first optical signal, and the semiconductor package further comprising:

a reflector disposed at a bottom surface of the lid structure, wherein the reflector is configured to provide an optical path of the first optical signal between the emitter and the receiver.

3. The semiconductor package of claim 1, further comprising a third die configured to generate a reference signal for the second die.

4. The semiconductor package of claim 1, wherein the first die has a first type of application and the second die has a second type of application different from the first type of application.

5. A semiconductor package, comprising:

a carrier; and a lid structure including a gas inlet and a gas outlet arranged along a first direction, wherein the lid structure and the carrier collectively define a first pathway connecting the gas inlet and the gas outlet, and wherein a first sidewall of the first pathway has a first height, and a second sidewall of the first pathway opposite to the first sidewall has a second height, and the first height being different from the second height; and a first die disposed in the first pathway, wherein a first lateral space between a vertical projection of the first die on the carrier and a vertical projection of the first sidewall on the carrier is different from a second lateral space between a vertical projection of the first die on the carrier and a vertical projection of the second sidewall on the carrier, wherein the first sidewall extends from the lid structure to the carrier, and wherein a bottom surface of the first sidewall is at a lower elevation than a top surface of the first die.

6. The semiconductor package of claim 5, further comprising an adhesive layer disposed at least in one of a first space between the first sidewall and the carrier or a second space between the second sidewall and the carrier.

7. The semiconductor package of claim 6, wherein the second height is greater than the first height.

* * * * *